United States Patent
Ying et al.

(10) Patent No.: US 7,190,757 B2
(45) Date of Patent: Mar. 13, 2007

(54) METHOD OF AND SYSTEM FOR COMPUTING EFFECTIVE ATOMIC NUMBER IMAGES IN MULTI-ENERGY COMPUTED TOMOGRAPHY

(75) Inventors: Zhengrong Ying, Wakefield, MA (US); Ram Naidu, Waban, MA (US); Sergey Simanovsky, Brookline, MA (US); Carl R. Crawford, Brookline, MA (US)

(73) Assignee: Analogic Corporation, Peabody, MA (US)

( * ) Notice: Subject to any disclaimer, the term of this patent is extended or adjusted under 35 U.S.C. 154(b) by 229 days.

(21) Appl. No.: 10/850,910

(22) Filed: May 21, 2004

(65) Prior Publication Data

US 2005/0259781 A1    Nov. 24, 2005

(51) Int. Cl.
*A61B 6/00* (2006.01)
(52) U.S. Cl. .............................. 378/5; 378/57
(58) Field of Classification Search .................. 378/5, 378/9, 57, 88
See application file for complete search history.

(56) References Cited

U.S. PATENT DOCUMENTS

| | | | |
|---|---|---|---|
| 5,182,764 A | 1/1993 | Peschmann et al. | |
| 5,367,552 A | 11/1994 | Peschmann et al. | |
| 5,473,657 A | 12/1995 | McKenna | |
| 5,490,218 A * | 2/1996 | Krug et al. | 382/100 |
| 5,642,393 A * | 6/1997 | Krug et al. | 378/57 |
| 5,661,774 A | 8/1997 | Gordon et al. | |
| 5,802,134 A | 9/1998 | Larson et al. | |
| 5,881,122 A | 3/1999 | Ruth et al. | |
| 5,887,047 A | 3/1999 | Ruth et al. | |
| 5,901,198 A | 5/1999 | Ruth et al. | |
| 5,909,477 A | 6/1999 | Ruth et al. | |
| 5,932,874 A | 8/1999 | Legg et al. | |
| 5,937,028 A | 8/1999 | Tybinkowski et al. | |
| 5,949,842 A | 9/1999 | Schafer et al. | |
| 5,970,113 A | 10/1999 | Ruth et al. | |
| 5,982,843 A | 11/1999 | Bailey et al. | |
| 5,982,844 A | 11/1999 | Tybinkowski et al. | |
| 6,025,143 A | 2/2000 | Simanovsky et al. | |
| 6,026,171 A | 2/2000 | Hiraoglu et al. | |
| 6,035,014 A | 3/2000 | Hiraoglu et al. | |
| 6,067,366 A | 5/2000 | Simanovsky et al. | |
| 6,075,871 A | 6/2000 | Simanovsky et al. | |
| 6,076,400 A | 6/2000 | Bechwati et al. | |
| 6,078,642 A | 6/2000 | Simanovsky et al. | |
| 6,088,423 A * | 7/2000 | Krug et al. | 378/57 |
| 6,091,795 A | 7/2000 | Schafer et al. | |
| 6,108,396 A | 8/2000 | Bechwati et al. | |
| 6,111,974 A | 8/2000 | Hiraoglu et al. | |
| 6,128,365 A | 10/2000 | Bechwati et al. | |
| 6,195,444 B1 | 2/2001 | Simanovsky et al. | |

(Continued)

*Primary Examiner*—Courtney Thomas
*Assistant Examiner*—Alexander Taningco
(74) *Attorney, Agent, or Firm*—McDermott, Will & Emery LLP

(57) ABSTRACT

A method of and a system for computing Z (effective atomic number) images from projection data are provided, wherein the projections are acquired using at least two x-ray spectra for a set of scanned objects, including a set of low energy projections and a set of high energy projections; the method comprises decomposing the low energy projections and high energy projections into photoelectric projections, reconstructing the photoelectric projections into photoelectric images, reconstructing one of the two sets of projections into CT images, and computing Z images from the CT images and the photoelectric images with parameters obtained from a calibration procedure.

14 Claims, 7 Drawing Sheets

U.S. PATENT DOCUMENTS

| | | |
|---|---|---|
| 6,256,404 B1 | 7/2001 | Gordon et al. |
| 6,272,230 B1 | 8/2001 | Hiraoglu et al. |
| 6,345,113 B1 | 2/2002 | Crawford et al. |
| 6,418,189 B1 * | 7/2002 | Schafer .................. 378/57 |
| 6,687,326 B1 | 2/2004 | Bechwati et al. |
| 6,721,387 B1 | 4/2004 | Naidu et al. |
| 2002/0097830 A1 * | 7/2002 | Raupach .................. 378/4 |

* cited by examiner

"METHOD OF AND SYSTEM FOR COMPUTING EFFECTIVE ATOMIC NUMBER IMAGES IN MULTI-ENERGY COMPUTED TOMOGRAPHY

RELATED APPLICATIONS

This patent application and/or patents are related to the following U.S. applications and/or issued U.S. patents, of the same assignee as the present application, the contents of which are incorporated herein in their entirety by reference:

"Nutating Slice CT Image Reconstruction Apparatus and Method," invented by Gregory L. Larson, et al., U.S. application Ser. No. 08/831,558, filed on Apr. 9, 1997, now U.S. Pat. No. 5,802,134, issued on Sep. 1, 1998;

"Computed Tomography Scanner Drive System and Bearing," invented by Andrew P. Tybinkowski, et al., U.S. application Ser. No. 08/948,930, filed on Oct. 10, 1997, now U.S. Pat. No. 5,982,844, issued Nov. 9, 1999;

"Air Calibration Scan for Computed Tomography Scanner with Obstructing Objects," invented by David A. Schafer, et al., U.S. application Ser. No. 08/948,937, filed on Oct. 10, 1997, now U.S. Pat. No. 5,949,842, issued Sep. 7, 1999;

"Computed Tomography Scanning Apparatus and Method With Temperature Compensation for Dark Current Offsets," invented by Christopher C. Ruth, et al., U.S. application Ser. No. 08/948,928, filed on Oct. 10, 1997, now U.S. Pat. No. 5,970,113, issued Oct. 19, 1999;

"Computed Tomography Scanning Target Detection Using Non-Parallel Slices," invented by Christopher C. Ruth, et al., U.S. application Ser. No. 08/948,491, filed on Oct. 10, 1997, now U.S. Pat. No. 5,909,477, issued on Jun. 1, 1999;

"Computed Tomography Scanning Target Detection Using Target Surface Normals," invented by Christopher C. Ruth, et al., U.S. application Ser. No. 08/948,929, filed on Oct. 10, 1997, now U.S. Pat. No. 5,901,198, issued on May 4, 1999;

"Parallel Processing Architecture for Computed Tomography Scanning System Using Non-Parallel Slices," invented by Christopher C. Ruth, et al., U.S. application Ser. No. 08/948,697, filed on Oct. 10, 1997, U.S. Pat. No. 5,887,047, issued on Mar. 23, 1999;

"Computed Tomography Scanning Apparatus and Method For Generating Parallel Projections Using Non-Parallel Slice Data," invented by Christopher C. Ruth, et al., U.S. application Ser. No. 08/948,492, filed on Oct. 10, 1997, now U.S. Pat. No. 5,881,122, issued on Mar. 9, 1999;

"Computed Tomography Scanning Apparatus and Method Using Adaptive Reconstruction Window," invented by Bernard M. Gordon, et al., U.S. application Ser. No. 08/949,127, filed on Oct. 10, 1997, now U.S. Pat. No. 6,256,404, issued Jul. 3, 2001;

"Area Detector Array for Computed Tomography Scanning System," invented by David A Schafer, et al., U.S. application Ser. No. 08/948,450, filed on Oct. 10, 1997, now U.S. Pat. No. 6,091,795, issued Jul. 18, 2000;

"Closed Loop Air Conditioning System for a Computed Tomography Scanner," invented by Eric Bailey, et al., U.S. application Ser. No. 08/948,692, filed on Oct. 10, 1997, now U.S. Pat. No. 5,982,843, issued Nov. 9, 1999;

"Measurement and Control System for Controlling System Functions as a Function of Rotational Parameters of a Rotating Device," invented by Geoffrey A. Legg, et al., U.S. application Ser. No. 08/948,493, filed on Oct. 10, 1997, now U.S. Pat. No. 5,932,874, issued Aug. 3, 1999;

"Rotary Energy Shield for Computed Tomography Scanner," invented by Andrew P. Tybinkowski, et al., U.S. application Ser. No. 08/948,698, filed on Oct. 10, 1997, now U.S. Pat. No. 5,937,028, issued Aug. 10, 1999;

"Apparatus and Method for Detecting Sheet Objects in Computed Tomography Data," invented by Muzaffer Hiraoglu, et al., U.S. application Ser. No. 09/022,189, filed on Feb. 11, 1998, now U.S. Pat. No. 6,111,974, issued on Aug. 29, 2000;

"Apparatus and Method for Eroding Objects in Computed Tomography Data," invented by Sergey Simanovsky, et al., U.S. application Ser. No. 09/021,781, filed on Feb. 11, 1998, now U.S. Pat. No. 6,075,871, issued on Jun. 13, 2000;

"Apparatus and Method for Combining Related Objects in Computed Tomography Data," invented by Ibrahim M. Bechwati, et al., U.S. application Ser. No. 09/022,060, filed on Feb. 11, 1998, now U.S. Pat. No. 6,128,365, issued on Oct. 3, 2000;

"Apparatus and Method for Detecting Sheet Objects in Computed Tomography Data," invented by Sergey Simanovsky, et al., U.S. application Ser. No. 09/022,165, filed on Feb. 11, 1998, now U.S. Pat. No. 6,025,143, issued on Feb. 15, 2000;

"Apparatus and Method for Classifying Objects in Computed Tomography Data Using Density Dependent Mass Thresholds," invented by Ibrahim M. Bechwati, et al., U.S. application Ser. No. 09/021,782, filed on Feb. 11, 1998, now U.S. Pat. No. 6,076,400, issued on Jun. 20, 2000;

"Apparatus and Method for Correcting Object Density in Computed Tomography Data," invented by Ibrahim M. Bechwati, et al., U.S. application Ser. No. 09/022,354, filed on Feb. 11, 1998, now U.S. Pat. No. 6,108,396, issued on Aug. 22, 2000;

"Apparatus and Method for Density Discrimination of Objects in Computed Tomography Data Using Multiple Density Ranges," invented by Sergey Simanovsky, et al., U.S. application Ser. No. 09/021,889, filed on Feb. 11, 1998, now U.S. Pat. No. 6,078,642, issued on Jun. 20, 2000;

"Apparatus and Method for Detection of Liquids in Computed Tomography Data," invented by Muzaffer Hiraoglu, et al., U.S. application Ser. No. 09/022,064, filed on Feb. 11, 1998, now U.S. Pat. No. 6,026,171, issued on Feb. 15, 2000;

"Apparatus and Method for Optimizing Detection of Objects in Computed Tomography Data," invented by Muzaffer Hiraoglu, et al., U.S. application Ser. No. 09/022,062, filed on Feb. 11, 1998, now U.S. Pat. No. 6,272,230, issued Aug. 7, 2001;

"Multiple-Stage Apparatus and Method for Detecting Objects in Computed Tomography Data," invented by Muzaffer Hiraoglu, et al., U.S. application Ser. No. 09/022,164, filed on Feb. 11, 1998, now U.S. Pat. No. 6,035,014, issued on Mar. 7, 2000;

"Apparatus and Method for Detecting Objects in Computed Tomography Data Using Erosion and Dilation of Objects," invented by Sergey Simanovsky, et al., U.S. application Ser. No. 09/022,204, filed on Feb. 11, 1998, now U.S. Pat. No. 6,067,366, issued on May 23, 2000;

"Apparatus and method for processing object data in computed tomography data using object projections," invented by Carl R. Crawford, et al, U.S. application Ser. No. 09/228,379, filed on Jan. 12, 1999, now U.S. Pat. No. 6,345,113, issued on Feb. 5, 2002;

"Apparatus and method for detecting concealed objects in computed tomography data," invented by Sergey Simanovsky, et al., U.S. application Ser. No. 09/228,380, filed on Jan. 12, 1999, now U.S. Pat. No. 6,195,444, issued on Feb. 27, 2001;

"Method of and system for correcting scatter in a computed tomography scanner," invented by Ibrahim M. Bechwati, et al, U.S. application Ser. No. 10/121,466, filed on Apr. 11, 2002, now U.S. Pat. No. 6,687,326, issued on Feb. 3, 2004;

"Method of and system for reducing metal artifacts in images generated by x-ray scanning devices," invented by Ram Naidu, et al, U.S. application Ser. No. 10/171,116, filed on Jun. 13, 2002, now U.S. Pat. No. 6,721,387, issued on Apr. 13, 2004;

"Decomposition of Multi-Energy Scan Projections using Multi-Step Fitting," invented by Ram Naidu, et al, U.S. application Ser. No. 10/611,572, filed on Jul. 1, 2003.

FIELD OF THE DISCLOSURE

The present disclosure relates to systems and methods for detecting materials of interest using X-ray radiation transmission to determine one or more physical characteristics of a material, and more particularly, to systems and methods for computing the effective atomic number (Z) of scanned materials used in such systems and methods.

BACKGROUND OF THE DISCLOSURE

Various X-ray baggage scanning systems are known for detecting the presence of explosives and other prohibited items in baggage, or luggage, prior to loading the baggage onto a commercial aircraft. A common technique of measuring a material's density is to expose the material to X-rays and to measure the amount of radiation absorbed by the material, the absorption being indicative of the density. Since many explosive materials may be characterized by a range of densities differentiable from that of other items typically found in baggage, explosives are generally amenable to detection by X-ray equipment.

Most X-ray baggage scanning systems in use today are of the "line scanner" type and include a stationary X-ray source, a stationary linear detector array, and a conveyor belt for transporting baggage between the source and detector array as the baggage passes through the scanner. The X-ray source generates an X-ray beam that passes through and is partially attenuated by the baggage and is then received by the detector array. During each measuring interval the detector array generates data representative of the integral of density of the planar segment of the baggage through which the X-ray beam passes, and this data is used to form one or more raster lines of a two-dimensional image. As the conveyor belt transports the baggage past the stationary source and detector array, the scanner generates a two-dimensional image representative of the density of the baggage, as viewed by the stationary detector array. The density image is typically displayed for analysis by a human operator.

Techniques using dual energy X-ray sources are known for providing additional information about a material's characteristics, beyond solely a density measurement. Techniques using dual energy X-ray sources involve measuring the X-ray absorption characteristics of a material for two different energy levels of X-rays. Depending upon the calibration of the scanner, dual energy measurements provide an indication of dual parameters of the material being scanned. For example, at one calibration setting, the dual parameters can be chosen to be the material's effective atomic number (Z is denoted as "effective atomic number") and the material's density. At another calibration setting, the dual parameters can be chosen to be the material's Photoelectric coefficients and the material's Compton coefficients. At yet another calibration setting, the dual parameters can be chosen to be an amount of a first material present (e.g., plastic) and an amount of a second material present (e.g., aluminum). Dual energy X-ray techniques for energy-selective reconstruction of X-ray Computer Tomography (hereinafter referred to as CT) images are described, for example, in Robert E. Alvarez and Albert Macovski, "Energy-selective Reconstructions in X-ray Computerized Tomography," Phys. Med. Biol. 1976, Vol. 21, No. 5, 733–744; and U.S. Pat. Nos. 4,029,963 and 5,132,998. One algorithm used to generate such dual parameters from dual energy X-ray projection data is known as the Alvarez/Macovski Algorithm (hereinafter referred to as AMA). Others are known in the art.

One proposed use for such dual energy techniques has been in connection with a baggage scanner for detecting the presence of explosives in baggage. Explosive materials are generally characterized by a known range of atomic numbers and are therefore amenable to detection by such dual energy X-ray sources. One such dual energy source is described in U.S. Pat. No. 5,661,774, entitled "Improved Dual Energy Power Supply," assigned to the present assignee and incorporated by reference. Other dual energy sources are known in the art.

Most explosives capable of significantly damaging an aircraft are sufficiently large in length, width, and height so as to be readily detectable by an X-ray scanner system regardless of the explosive's orientation within the baggage. Plastic explosives, however, present a particular challenge to baggage scanning systems. Due to their moldable nature, plastic explosives may be formed into geometric shapes that are difficult to detect. A plastic explosive powerful enough to damage an aircraft may be formed into a relatively thin sheet that is extremely small in one dimension and is relatively large in the other two dimensions. The detection of plastic explosives may be difficult because it may be difficult to see the explosive material in the image, particularly when the material is disposed so that the thin sheet is parallel to the direction of the X-ray beam as the sheet passes through the system.

Thus, detection of suspected baggage requires very attentive operators. The requirement for such attentiveness can result in greater operator fatigue, and fatigue as well as any distractions can result in a suspected bag passing through the system undetected. Accordingly, a great deal of effort has been made to design a better baggage scanner. Such designs, for example, have been described in U.S. Pat. No. 4,759,047 (Donges et al.); U.S. Pat. No.4,884,289 (Glockmann et al.); U.S. Pat. No.5,132,988 (Tsutsui et al.); U.S. Pat. No. 5,182,764 (Peschmann et al.); U.S. Pat. No.5,247,561 (Kotowski); U.S. Pat. No.5,319,547 (Krug et al.); U.S. Pat. No. 5,367,552 (Peschmann et al.); U.S. Pat. No. 5,490,218 (Krug et al.) and German Offenlegungsschrift DE 31 503 06 A1 (Heimann GmbH).

At least one of these designs, described in U.S. Pat. No. 5,182,764 (Peschmann et al.) and U.S. Pat. No.5,367,552 (Peschmann et al.) (hereinafter the '764 and '552 patents), has been commercially developed and is referred to hereinafter as the "Invision Machine." The Invision Machine includes a CT scanner of the third generation type, which typically includes an X-ray source and an X-ray detector system secured respectively to diametrically opposite sides of an annular-shaped platform or disk. The disk is rotatably mounted within a gantry support so that in operation the disk continuously rotates about a rotation axis while X-rays pass from the source through an object positioned within the opening of the disk to the detector system.

The detector system can include a linear array of detectors disposed as a single row in the shape of a circular arc having a center of curvature at the focal spot of the X-ray source, i.e., the point within the X-ray source from which the X-rays emanate. The X-ray source generates a fan shaped beam, or fan beam, of X-rays that emanates from the focal spot, passes through a planar imaging field, and is received by the detectors. The CT scanner includes a coordinate system defined by X-, Y- and Z-axes, wherein the axes intersect and are all normal to one another at the center of rotation of the disk as the disk rotates about the rotation axis. This center of rotation is commonly referred to as the "isocenter." The Z-axis is defined by the rotation axis and the X- and Y-axes are defined by and lie within the planar imaging field. The fan beam is thus defined as the volume of space defined between a point source, i.e., the focal spot, and the receiving surfaces of the detectors of the detector array exposed to the X-ray beam. Because the dimension of the receiving surfaces of the linear array of detectors is relatively small in the Z-axis direction the fan beam is designed to be relatively thin in the Z-axis direction. Each detector generates an output signal representative of the intensity of the X-rays incident on that detector. Since the X-rays are partially attenuated by all the mass in their path, the output signal generated by each detector is representative of the density of all the mass disposed in the imaging field between the X-ray source and that detector.

As the disk rotates, the detector array is periodically sampled, and for each measuring interval each of the detectors in the detector array generates an output signal representative of the density of a portion of the object being scanned during that interval. The collection of all of the output signals generated by all the detectors in a single row of the detector array for any measuring interval is referred to as a "projection," or equivalently as a "view," and the angular orientation of the disk (and the corresponding angular orientations of the X-ray source and the detector array) during generation of a projection is referred to as the "projection angle." At each projection angle, the path of the X-rays from the focal spot to each detector, called a "ray," increases in cross section from an appropriate point source to the receiving surface area of the detector, and thus is thought to magnify the density measurement because the receiving surface area of the detector area is larger than any cross sectional area of the object through which the ray passes.

As the disk rotates around the object being scanned, the scanner generates a plurality of projections at a corresponding plurality of projection angles. Using well known algorithms a CT image of the object may be generated from all the projection data collected at each of the projection angles. The CT image is representative of the density of a two dimensional "slice" of the object through which the fan beam has passed during the rotation of the disk through the various projection angles. The resolution of the CT image is determined in part by the width of the receiving surface area of each detector in the plane of the fan beam, the width of the detector being defined herein as the dimension measured in the same direction as the width of the fan beam, while the length of the detector is defined herein as the dimension measured in a direction normal to the fan beam parallel to the rotation or Z-axis of the scanner. In general, the resolution of the CT image is inversely proportional to the width of the receiving surface of each detector in the plane of the fan beam.

Referring to the drawings, FIGS. 1, 2 and 3 show perspective, end cross-sectional and radial cross-sectional views, respectively, of a typical baggage scanning system 100, which includes a conveyor system 110 for continuously conveying baggage or luggage 112 in a direction indicated by arrow 114 through a central aperture of a CT scanning system 120. The conveyor system includes motor driven belts for supporting the baggage. Conveyer system 110 is illustrated as including a plurality of individual conveyor sections 122; however, other forms of conveyor systems may be used.

The CT scanning system 120 includes an annular shaped rotating platform, or disk, 124 disposed within a gantry support 125 for rotation about a rotation axis 127 (shown in FIG. 3) that is preferably parallel to the direction of travel 114 of the baggage 112. Disk 124 is driven about rotation axis 127 by any suitable drive mechanism, such as a belt 116 and motor drive system 118, or other suitable drive mechanism, such as the one described in U.S. Pat. No. 5,473,657 issued Dec. 5, 1995 to Gilbert McKenna, entitled "X-ray Tomographic Scanning System," which is assigned to the present assignee and which is incorporated herein in its entirety by reference. Rotating platform 124 defines a central aperture 126 through which conveyor system 110 transports the baggage 112.

The system 120 includes an X-ray tube 128 and a detector array 130 which are disposed on diametrically opposite sides of the platform 124. The detector array 130 is preferably a two-dimensional array, such as the array described in U.S. Pat. No. 6,091,795 entitled, "Area Detector Array for Computed Tomography Scanning System." Other suitable arrays are known in the art. The system 120 further includes a data acquisition system (DAS) 134 for receiving and processing signals generated by detector array 130, and an X-ray tube control system 136 for supplying power to, and otherwise controlling the operation of, X-ray tube 128. The system 120 is also preferably provided with a computerized system (not shown) for processing the output of the data acquisition system 134 and for generating the necessary signals for operating and controlling the system 120. The computerized system can also include a monitor for displaying information including generated images. System 120 also includes shields 138, which may be fabricated from lead, for example, for preventing radiation from propagating beyond gantry 125.

The X-ray tube 128 may generate a pyramidically shaped beam, often referred to as a "cone beam," 132 of X-rays that pass through a three dimensional imaging field, through which conveying system 110 transports baggage 112. After passing through the baggage disposed in the imaging field, detector array 130 receives cone beam 132 and generates signals representative of the densities of exposed portions of baggage 112. The beam therefore defines a scanning volume of space. Platform 124 rotates about its rotation axis 127, thereby transporting X-ray source 128 and detector array 130 in circular trajectories about baggage 112 as the conveyor system 110 continuously transports baggage through central aperture 126, so as to generate a plurality of projections at a corresponding plurality of projection angles. When dual energy scanning mode is configured, the control system 136 supplies modulated high voltages with respect to alternating projection angles to the X-ray tube 128. The detector array 130 then receives data corresponding to high energy and low energy X-ray spectra in alternating projection angles.

Post-reconstruction analysis and pre-reconstruction analysis are the two prior art techniques generally recognized for using dual energy X-ray sources in materials analysis (e.g., in a baggage scanner for detecting the presence of explosives in baggage). In post-reconstruction analysis, the signal flow is as shown in FIG. 4. The scanner 120 is typically similar to the one shown in FIGS. 1–3 and has an X-ray source capable of producing a fan or cone beam at two distinct energy levels (i.e., dual energy). The DAS 134 gathers signals generated by detector array 130 at discrete angular positions of the rotating platform 124, and passes the signals to the pre-processing element 206. The pre-processing element 206 re-sorts the data it receives from the DAS 134 in order to optimize the sequence for the subsequent mathematical processing. The pre-processing element 206 also corrects the data from the DAS 134 for detector temperature, intensity of the primary beam, gain and offset, and other deterministic error factors. Finally, the pre-processing element 206 extracts data corresponding to high-energy views and routes it to a high energy path 208, and routes the data corresponding to low-energy views to a low energy path 210. A first reconstruction computer 218 receives the projection data from the high-energy path 208 and generates a CT image $I_H$ 226 corresponding to the high-energy series of projections. A second reconstruction computer 220 receives the projection data from the low-energy path 210 and generates a CT image $I_L$ 224 corresponding to the low-energy series of projections. A post-processing element 230 receives the high energy CT image 226 and the low-energy CT image 224 and performs voxel-by-voxel processing to yield the Z (effective atomic number) image $I_z$ 232. The Z image 232 and the high energy CT image 226 can be provided to operators on a display 240, and both images can be used for automatic explosive detection in 238 as well. The images from the post-reconstruction analysis usually do not yield accurate estimates of the material's effective atomic number, and suffer low SNR (Signal to Noise Ratio) and many artifacts as well.

In pre-reconstruction analysis, the signal flow is as shown in FIG. 5. As is described herein for pre-reconstruction analysis, the dual energy decomposition computer 212 receives the projection data on the high energy path 208 and the low energy path 210 and performs the Alvarez/Macovski Algorithm to produce a first stream of projection data $A_c$ 214, which is dependent on a first parameter of the material being scanned and a second stream of projection data $A_p$ 216 which is dependent on a second parameter of the material scanned. The first material parameter is often the Compton coefficient $a_c$ and the second material parameter is often photoelectric coefficient $a_p$. A first reconstruction computer 219 receives the first stream of projection data 214 and generates a Compton image $I_c$ 227 from the series of projections corresponding to the first material parameter. A second reconstruction computer 221 receives the second stream of projection data 216 and generates a photoelectric image $I_p$ 225 from the series projections corresponding to the second material parameter. The third reconstruction computer 218 receives the stream of projection data 208 and generates a CT image $I_H$ 226. The two images 225 and 227 are processed in the post-processing element 230 to yield a Z image $I_z$ 232. The CT image 226 and the Z image 232 can be provided to operators on a display 240, and both images can be used for automatic explosive detection in 238 as well. The pre-reconstruction analysis yields better estimates of material's effective atomic number than the post-reconstruction analysis. However the pre-reconstruction analysis requires one more reconstruction computer than the post-reconstruction analysis.

Various approaches have been used for decomposition of the input projection data $P_L$ and $P_H$ into Compton projections $A_c$ and photoelectric projections $A_p$. For example, the AMA method approximates $P_L$ and $P_H$ using polynomial functions in terms of $A_c$ and $A_p$. The coefficients of the polynomial functions are determined through a calibration procedure as follows. By measuring the projections values of the combination of various thicknesses of two known materials, the coefficients can be calculated through a polynomial least squares fitting between the measured and modeled $P_L$ and $P_H$. Once the coefficients the polynomial functions are determined, the decomposition of the Compton and Photoelectric projections $A_c$ and $A_p$ from projections $P_L$ and $P_H$ is usually solved using the Newton-Raphson method.

Another prior art method of performing decomposition is the direct approximation method, discussed in L. A. Lehmann, R. E. Alvarez, A. Macovski, W. R. Brody, N. J. Pelc, S. J. Riederer, and A. L. Hall, *Generalized Image Combinations In Dual KVP Digital Radiography*, Med. Phys. 8, 659–667 (1981). In the direct approximation method, $A_c$ and $A_p$ are approximated as polynomial functions in terms of $P_L$ and $P_H$. The coefficients of the polynomial functions in the direct approximation method are determined through a calibration procedure by measuring the projections values of the combination of various thicknesses of two known materials.

In yet another prior art method, decomposition is accomplished using iso-transmission lines, described K. Chuang and H. K. Huang, *A Fast Dual-Energy Computational Method Using Isotransmission Lines and Tables*, Med. Phys. 14, 186–192 (1987). According to this method, for a given projection value, an iso-transmission line is represented by a linear equation in two basis functions. The iso-transmission line method requires a large amount of calibration data. Further, the iso-transmission lines become increasingly nonlinear as the projection value increases. In such a situation, the linear equations are not valid and the method causes large approximation errors.

The pre-reconstruction analysis usually yields better estimates of the material's effective atomic number than the post-reconstruction analysis. However, the pre-reconstruction analysis as shown in FIG. 5 requires one more reconstruction computer than the post-reconstruction analysis as shown in FIG. 4. Note that the reconstruction computers are the most expensive parts among all the subsystems for processing projection data from DAS 134 to post-processing 230.

The effective atomic number (Z) is the estimate of the hypothetical single element that will give the same X-ray attenuation as the substance being evaluated. In the pre-reconstruction analysis, the Z images are derived from reconstructed Compton images and photoelectric images with the pre-reconstruction dual energy decomposition algorithms, such as in AMA method.

SUMMARY OF THE DISCLOSURE

In accordance with the present disclosure, an algorithm for computing Z images using photoelectric images and CT images is provided. The algorithm eliminates the reconstruction of the Compton images, and therefore reduces the computational cost for the scanner system. The resulting Z images yields an approximate Z measurement of scanned objects.

In accordance with the present disclosure, an algorithm for computing Z images is provided with better image quality and reduced computational cost. The Z images provide additional information besides the CT image, and are useful for threat detection, such as explosive detection, and weapon detection. The algorithm in accordance with the present disclosure processes projection data acquired using at least two x-ray spectra for a scanned object, including a set of low energy projections $P_L$ and a set of high energy projections $P_H$, to yield Z images.

The algorithm may include a pre-reconstruction dual energy decomposition procedure wherein, for each pair of $P_L$ and $P_H$, the photoelectric projections $A_P$ are computed, but the Compton projections $A_c$ are not computed. In one embodiment, a table-look-up method with linear interpolation is used to obtain $A_P$ for each pair of $P_L$ and $P_H$. A two-dimensional table containing pairs of discrete $P_L$ and $P_H$ is generated offline. The method described in the assignees' "Decomposition of Multi-Energy Scan Projections using Multi-Step Fitting" by Naidu, et. al. U.S. application Ser. No. 10/611,572, filed on Jul. 1, 2003, incorporated herein by reference, is preferably used to compute the table. Other pre-reconstruction dual energy decomposition methods, such as AMA method, can also be used.

In one embodiment, the algorithm may include reconstructing the high energy projection data into CT images. Low energy projection data can also be reconstructed into CT images. The algorithm may also include reconstructing the photoelectric projection data into photoelectric images.

In accordance with the disclosure, the algorithm may include a nonlinear spectral correction in reconstructing CT images. A nonlinear polynomial function with parameters the same or different for all the detectors and views can be used.

In another embodiment, the algorithm may include generating a Z image from the reconstructed CT image and the photoelectric image on a pixel-by-pixel basis with parameters obtained from a calibration procedure.

In one embodiment, a calibration procedure is used to derive parameters for computing a Z image. Two materials with known effective atomic numbers are scanned to generate Z images. Regions of interest containing only one of the two scanned materials are identified. Mean values in the regions of interest of the Z images are computed. Parameters are computed from the mean values and known effective atomic numbers of the two scanned materials. More than two materials with known effective atomic numbers can also be used to derive the parameters.

BRIEF DESCRIPTION OF THE DRAWINGS

The drawing figures depict preferred embodiments by way of example, not by way of limitations. In the figures, like reference numerals refer to the same or similar elements.

DETAILED DESCRIPTION OF THE DRAWINGS

In accordance with the present disclosure, an algorithm for computing Z images using photoelectric images and CT images is provided. The algorithm eliminates the reconstruction of the Compton images, and therefore reduces the computational cost for the scanner system. The resulting Z images yield an approximate Z measurement of scanned objects.

The Compton image measures the Compton coefficients of the scanned material, and the CT image yields CT numbers of the scanned material. The CT number is approximately a scaled version of the Compton coefficient as shown below, therefore using the CT image to replace the Compton image for computing a Z image yields an approximate Z measurement of scanned objects.

The CT image generated from the poly-energetic X-ray source with the beam hardening correction approximately measures the material attenuation as if the X-ray source were mono-energetic at the mean energy E of the poly-energetic X-ray source. Denote $I_H$ as the CT number from the CT image, and $\mu(E)$ as a material's attenuation function in terms of X-ray photon energy E, then, $$I_H = S\mu(E) \tag{a}$$

where S is a constant, which usually scales the attenuation of water to 1000 Hounsfield Units (HU). The mean energy level of the poly-energetic X-ray source is about 80 keV for 160 kV DC input voltage on the assignee's scanner as described before.

As described in Robert E. Alvarez and Albert Macovski, "Energy-selective Reconstructions in X-ray Computerized Tomography," Phys. Med. Biol. 1976, Vol. 21, No. 5, 733–744, a material's X-ray attenuation function $\mu(E)$ can be modeled as follows, $$\mu(E) = a_p f_p(E) + a_c f_{KN}(E)$$

where $f_p(E) = E^{-3}$, $f_{KN}(E)$ is the well-known Klein-Nishina function, $a_c$ is the Compton coefficient, and $a_p$ is the photoelectric coefficient.

Since the photoelectric effect $a_p f_p(E)$ is a small part of the total attenuation $\mu(E)$, for example, only 2% for water at E=80 keV, $\mu(E)$ can be approximated by the Compton effect as follows, $$\mu(E) \approx a_c f_{KN}(E) \tag{b}$$

Relating Equations (a) and (b) together, the CT number $I_H$ is a scaled version of the Compton coefficient as follows, $$I_H \approx a_c \underbrace{S f_{KN}(E)}_{\text{constant}} \tag{c}$$

Equation (c) establishes the theoretical support of replacing the Compton image using the CT image to compute the Z image, resulting in reduced computational cost for baggage screening system using dual energy CT scanners.

Figure 1:
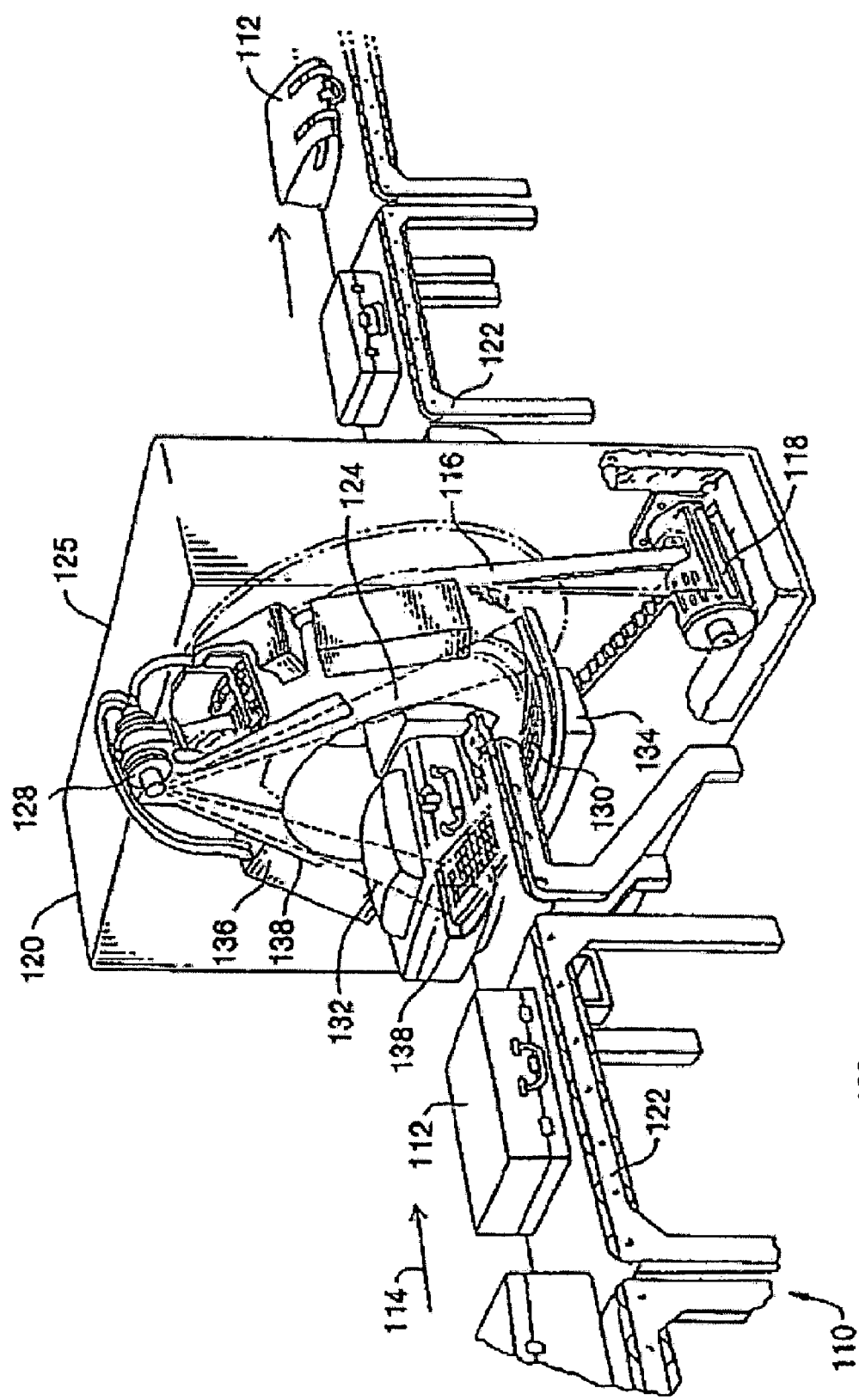
FIG. 1 is a perspective view of a baggage scanning system, known in the prior art.
Figure 6:
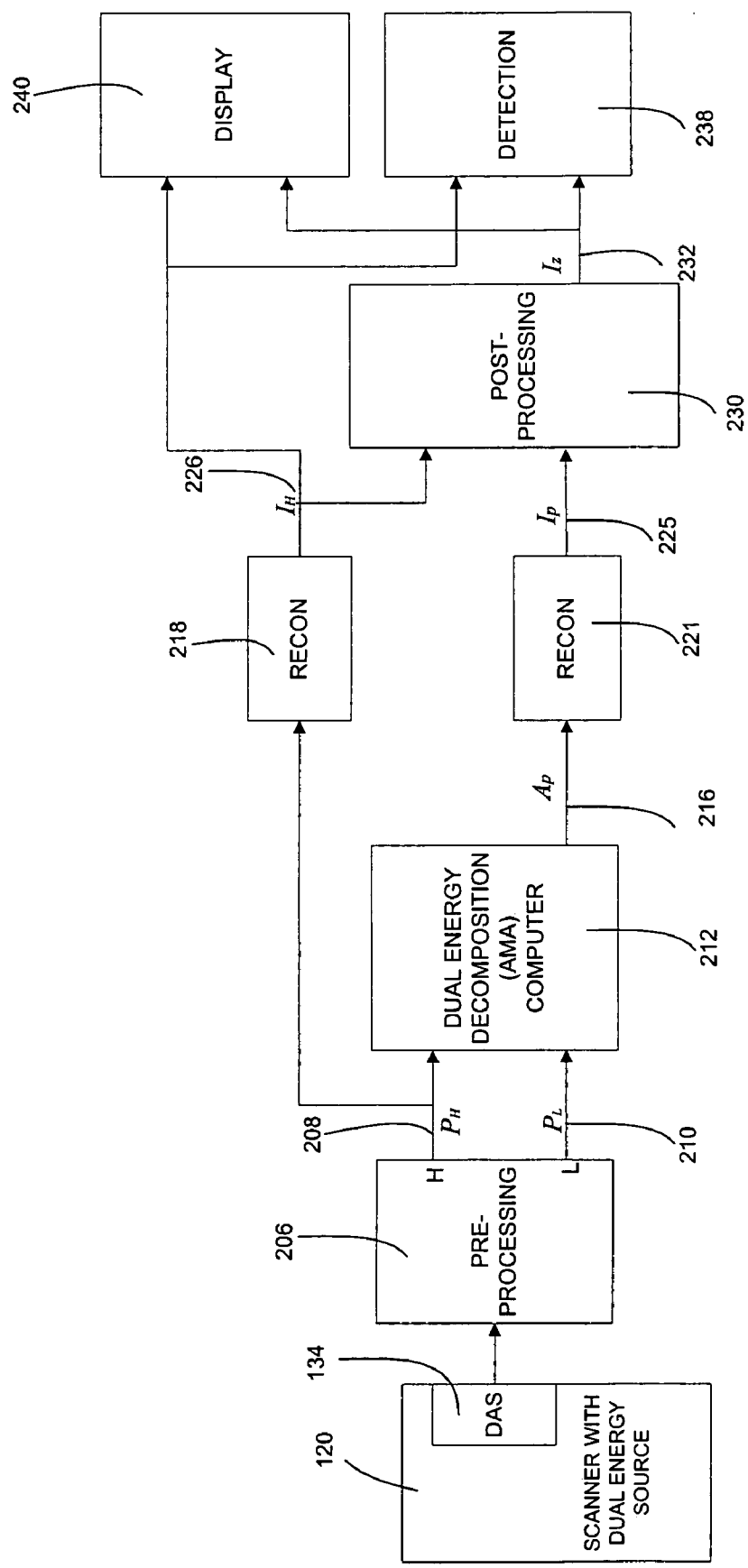
FIG. 6 is a signal flow diagram of a system, like FIG. 5, capable of performing pre-reconstruction analysis of the present disclosure, useful in the system of FIG. 1.

FIG. 6 illustrates the signal and data flow of the scanner system for explosive detection for the checked baggage at an airport, for example. The scanner 120 is typically similar to the one shown in FIG. 1 and has an X-ray source capable of producing a fan beam at two distinct energy levels (i.e., dual energy). The DAS 134 gathers signals generated by detector array 130 at discrete angular positions of the rotating platform 124, and passes the signals to the pre-processing element 206. The pre-processing element 206 re-sorts the data it receives from the DAS 134 in order to optimize the sequence for the subsequent mathematical processing. The pre-processing element 206 also corrects the data from the DAS 134 for detector temperature, intensity of the primary beam, gain and offset, and other deterministic error factors. Finally, the pre-processing element 206 extracts data corresponding to high-energy views and routes it to a high energy path 208, and routes the data corresponding to low-energy views to a low energy path 210. The dual energy decomposition computer 212 receives the projection data on the high energy path 208 and the low energy path 210 and performs a dual energy decomposition to produce photoelectric projections 216. A first reconstruction computer 221 receives the stream of the photoelectric projection data 216 and generates a photoelectric image $I_p$ 225. The second reconstruction computer 218 receives the stream of projection data 208 and generates a CT image $I_H$ 226. These two images 225 and 226 are processed in the post-processing element 230 to yield a Z image $I_z$. The element 240 displays the CT image 226 and Z image 232 to operators, and the element 238 uses the Z image 232 and the CT image 226 for automatic explosive detection.

Figure 2:
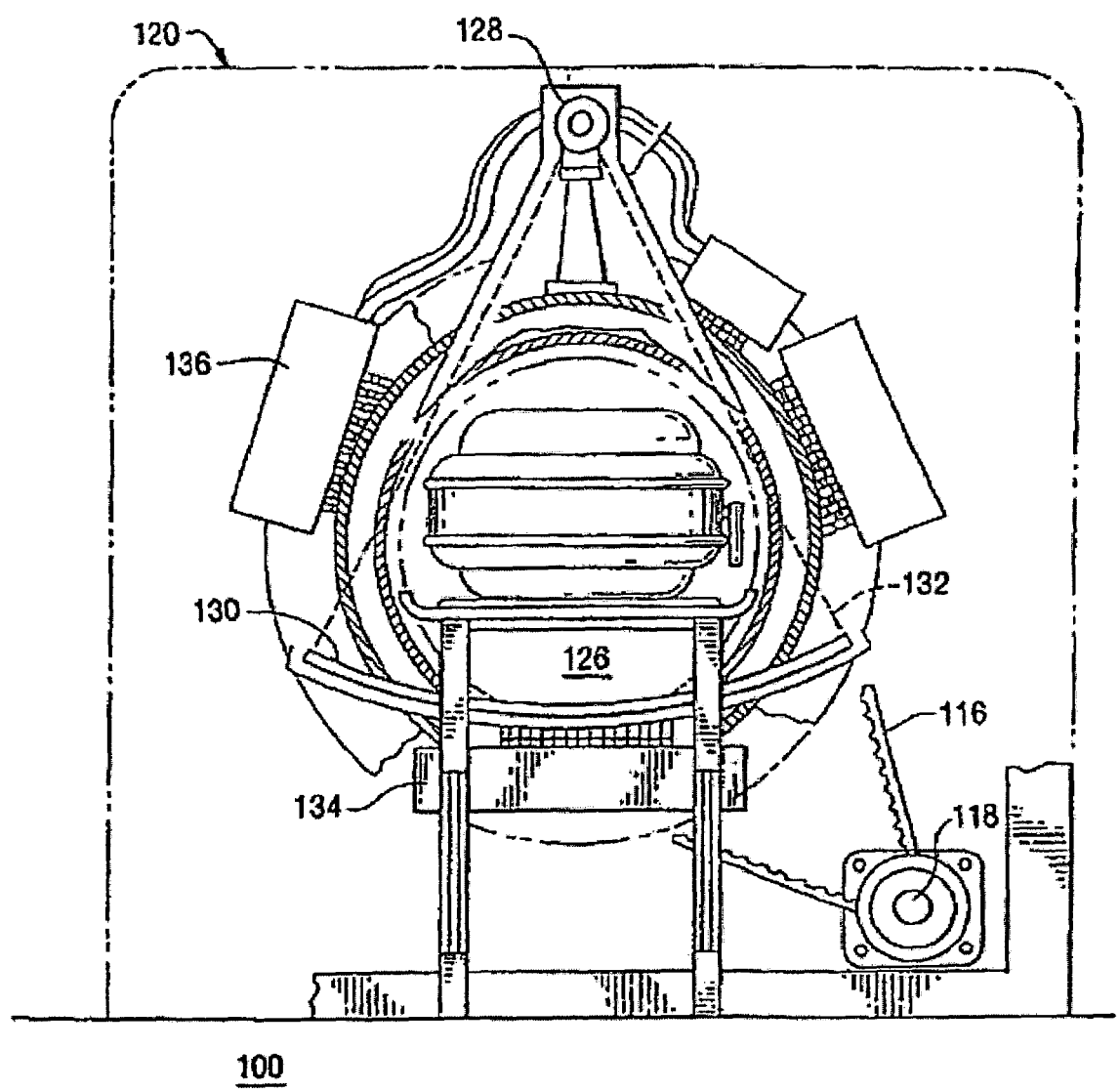
FIG. 2 is a cross-sectional end view of the system of FIG. 1.
Figure 3:
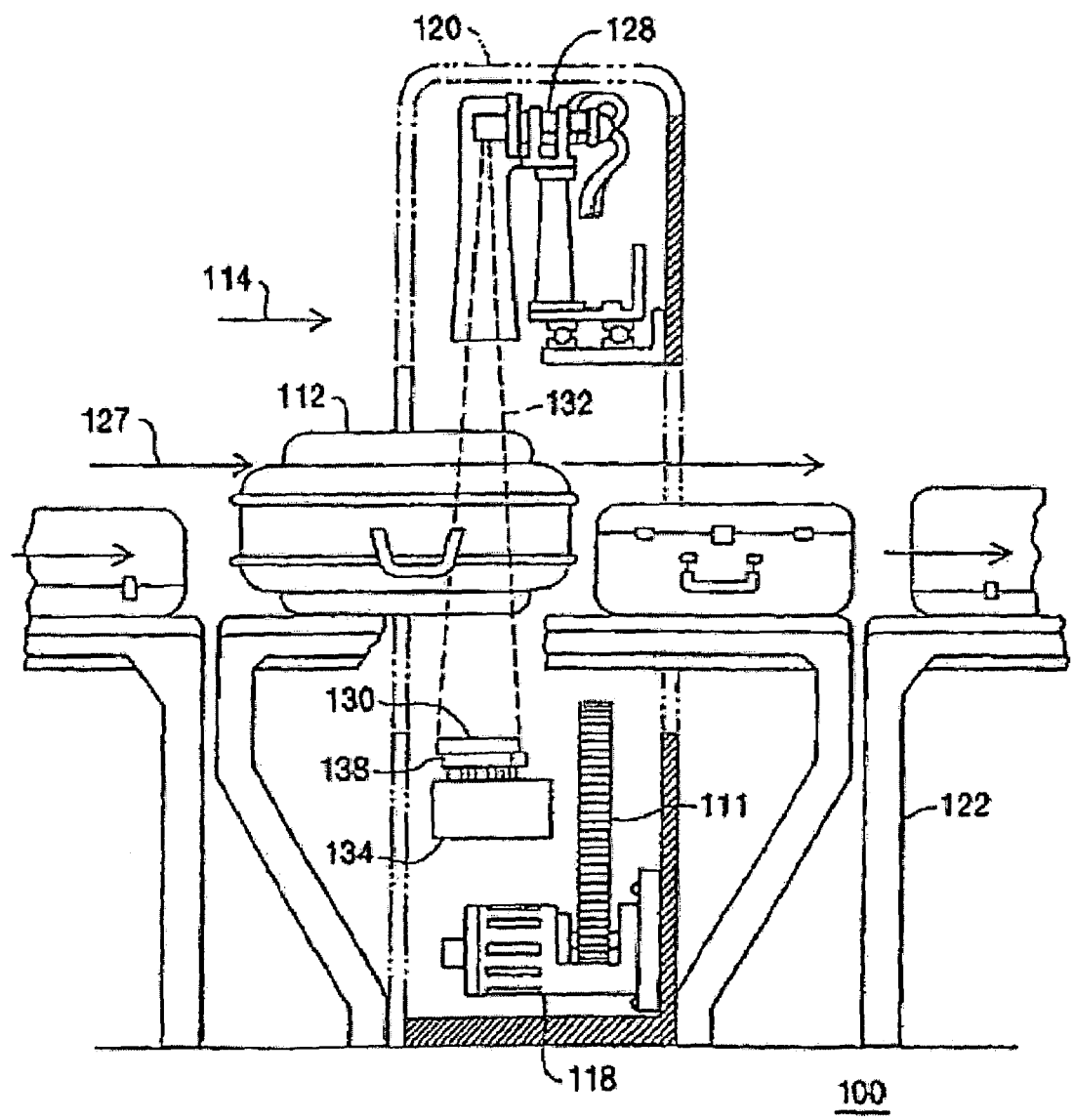
FIG. 3 is a cross-sectional radial view of the system of FIG. 1.
Figure 4:
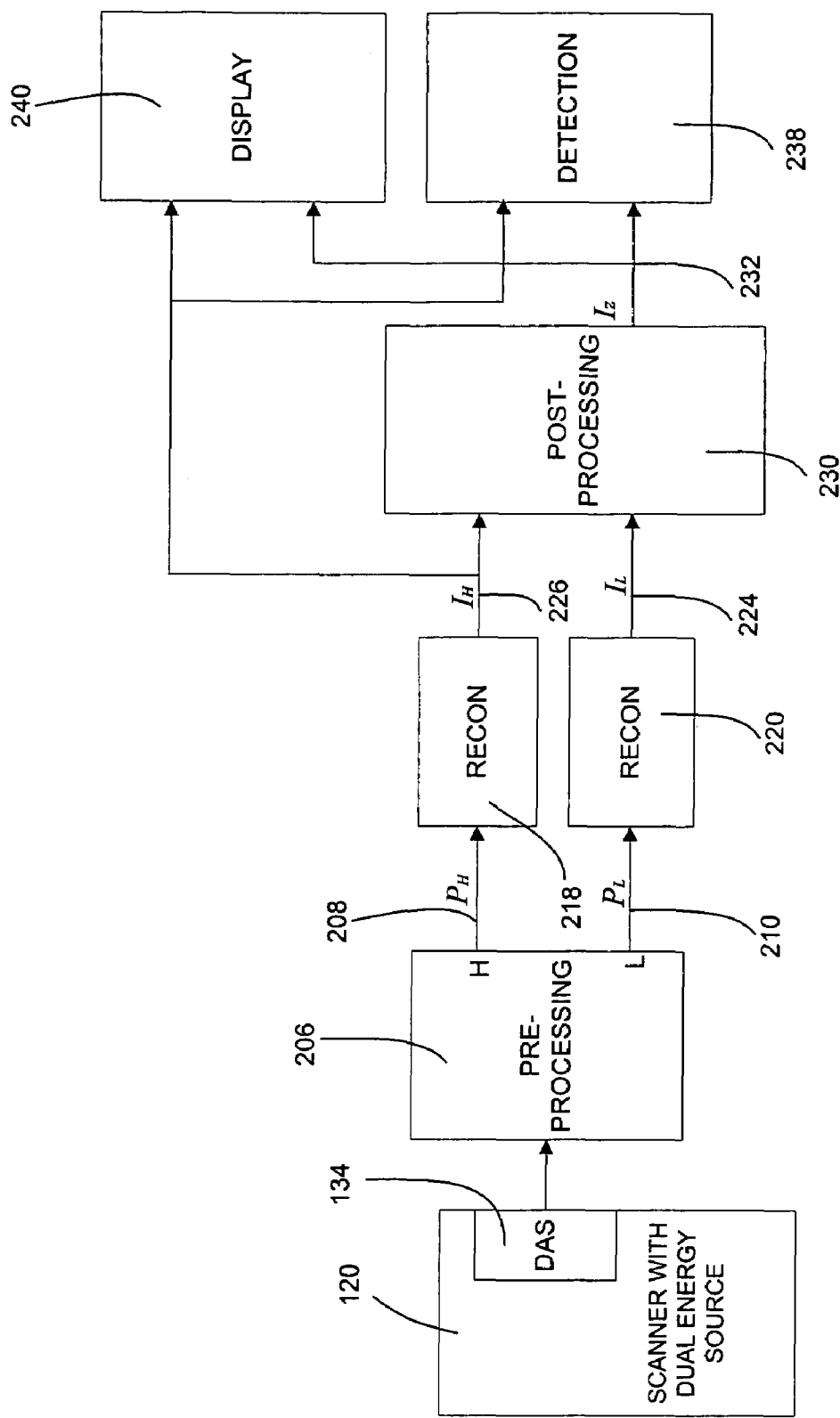
FIG. 4 is a signal flow diagram of a system capable of performing post-reconstruction analysis, useful in the system of FIG. 1.
Figure 5:
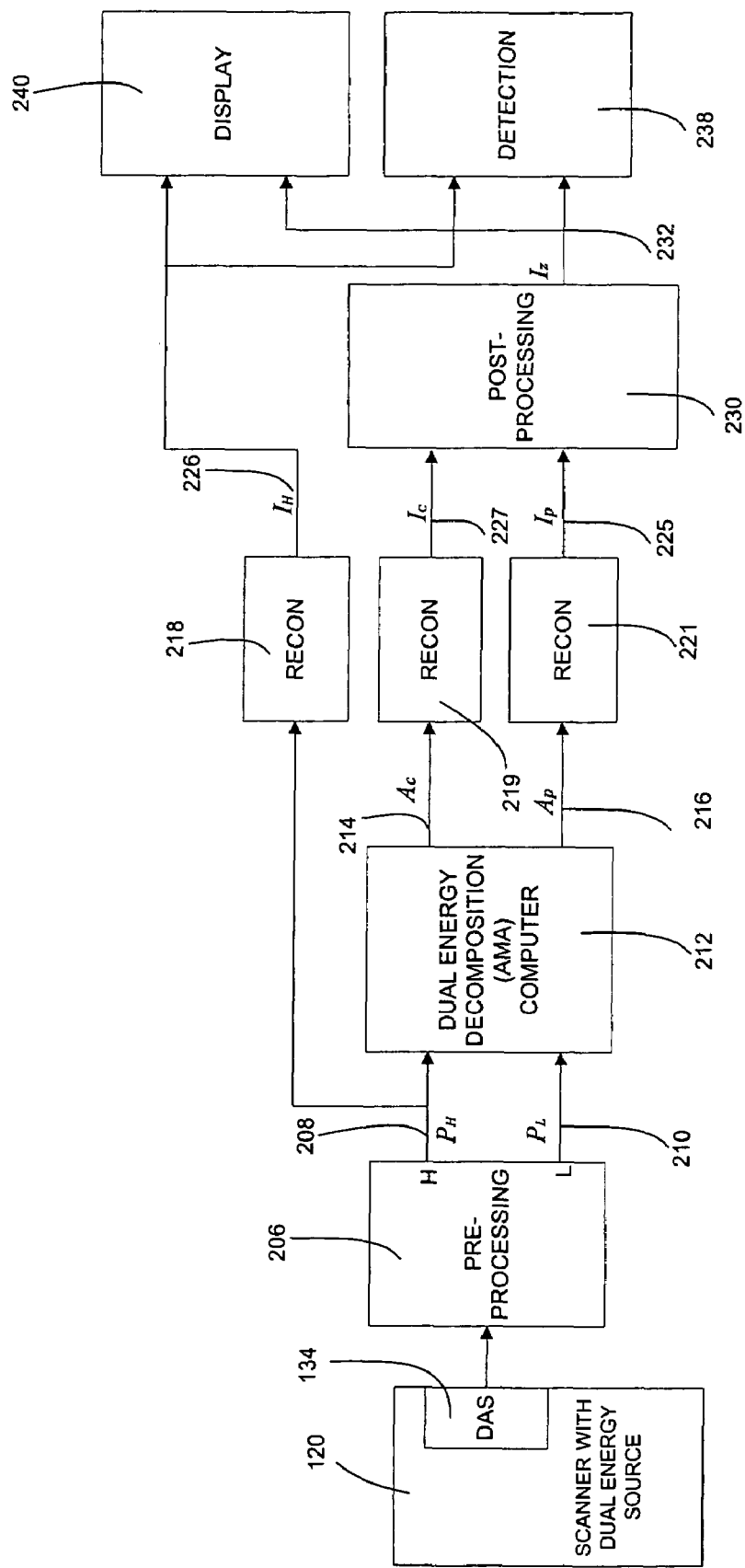
FIG. 5 is a signal flow diagram of a system capable of performing pre-reconstruction analysis, useful in the system of FIG. 1.
Figure 7:
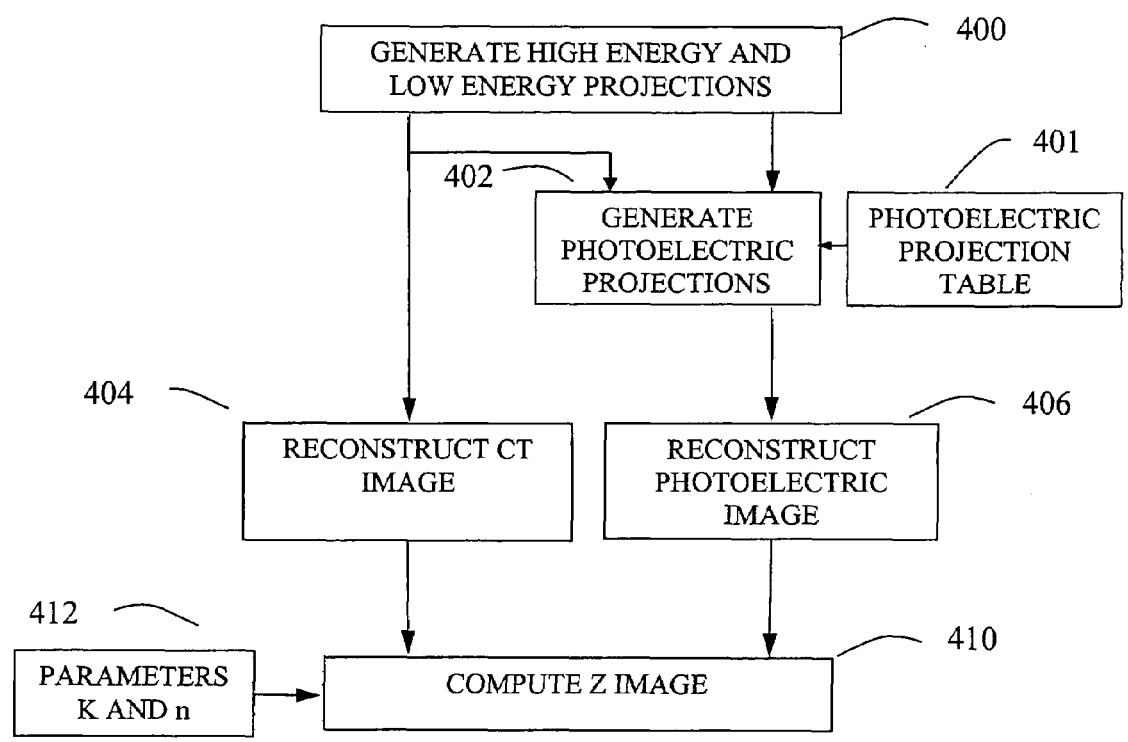
FIG. 7 contains a top-level flow diagram which illustrates the logical flow of one embodiment of computing the Z image of the present disclosure.

In accordance with the present disclosure, an algorithm for computing Z images using reconstructed photoelectric images and CT images is provided. This embodiment is described with respect to a CT scanner with an x-ray source and detector configuration, such as that shown and described with respect to FIGS. 1, 2, and 3. The preferred embodiment for computing the Z images comprises:

Generating projection data including a set of high energy projections and a set of low energy projections;

Reconstructing CT images from high energy projections;

Obtaining photoelectric projections from a pre-reconstruction dual energy decomposition;

Reconstructing photoelectric images from the photoelectric projections;

Computing the Z images from the CT images and the photoelectric images;

FIG. 7 contains the flow chart of the method in accordance with the present disclosure, and is used preferably to describe the details of the preferred method. In Step 400, the scanner source generates a low energy spectrum and a high energy spectrum. $I_L$ and $I_H$ are the corresponding x-ray intensities that are detected by the detectors when the object is scanned. $I_{oL}$ and $I_{oH}$ are the corresponding x-ray intensities that are detected in the absence of any object. $P_L$ and $P_H$ are the corresponding low and high energy projections that are computed, given by:

$$P_L = -\ln\left(\frac{I_L}{I_{oL}}\right)$$

$$P_H = -\ln\left(\frac{I_H}{I_{oH}}\right)$$

Note that there are typically more well-known steps involved in correcting the above computed $P_L$ and $P_H$ to yield satisfactory image qualities.

A two-dimensional photoelectric projection table $A_p^t(l,h)$, $l=0, \ldots, N_l-1$, $h=0, \ldots N_h-1$ with $N_l \times N_h$ entries, is computed offline and stored at Step 401. An entry $A_p^t(l,h)$ of the photoelectric projection table corresponds to a pair of low energy projection value $l\delta_l$ and high energy projection value $h\delta_h$. $N_l$, $N_h$, $\delta_l$, and $\delta_h$ are experimentally determined to cover the ranges of the high energy and low energy projections, for example, $N_l=N_h=240$, $\delta_l=\delta_h=0.05$ yields satisfactory results for the assignee's scanner as described before. For a given pair of low energy projection value $l\delta_l$ and high energy projection value $h\delta_h$, the method described in the assignees' "Decomposition of Multi-Energy Scan Projections using Multi-Step Fitting" by Naidu, et. al. U.S. application Ser. No. 10/611,572, filed on Jul. 1, 2003, incorporated herein by reference, is preferably used to compute $A_p^t(l,h)$.

Next in Step 402, for each pair of low energy projection $P_L$ and high energy projection $P_H$ from Step 400, the photoelectric projection $A_p$ is computed from the two-dimensional table $A_p^t(l, h)$ stored in a table at Step 401. Two-dimensional linear interpolation is preferably used with the table look-up as follows, $$A_p = (1-w_1)\lfloor(1-w_2)A_p^t(l,h)+w_2 A_p^t(l,h+1)\rfloor + w_1\lfloor(1-w_2)A_p^t(l+1,h)+w_2 A_p^t(l+1,h+1)\rfloor$$

where $$l = \left\lfloor \frac{P_L}{\delta_l} \right\rfloor, \ h = \left\lfloor \frac{P_H}{\delta_h} \right\rfloor, \ w_1 = \frac{P_L}{\delta_l} - l, \ w_2 = \frac{P_H}{\delta_h} - h$$

Note that $\lfloor x \rfloor$ is the maximum integer which is not greater than x.

At step 404, a CT image is reconstructed from the high energy projections. The method described in U.S. Pat. No. 5,802,134 (Larson, et al.), and incorporated herein by reference, is preferably used to reconstruct the CT images from the high energy projections $P_H$. The reconstructed CT image consists of a plurality of voxels, each of which has a value of CT number representing the density of scanned objects. Denote $I_H(x, y, z)$ as the reconstructed CT image, where x, y and z follow the scanner's coordinate system defined previously.

In the reconstruction of CT images, a nonlinear correction called beam hardening correction, described in Avinash C. Kak and Malcolm Slaney, *Principles of Computerized Tomographic Imaging*, IEEE Press, 1988, is preferably used to compensate for the poly-energetic spectrum of the X-ray source.

In step 406, a photoelectric image is reconstructed from the photoelectric projections. The method described in U.S. Pat. No. 5,802,134 (Larson, et al.), and incorporated herein by reference, is preferably used to reconstruct the photoelectric images from the photoelectric projections $A_p$. The reconstructed photoelectric image consists of a plurality of voxels, each of which has a value of photoelectric coefficient representing one of the properties of scanned objects. Denote $I_p(x,y,z)$ as the reconstructed photoelectric image, where x, y and z follow the scanner's coordinate system defined previously.

Next in step 410, a Z image is computed from the reconstructed photoelectric image and the reconstructed CT image on pixel-by-pixel basis with the parameters K and n supplied from Item 412. Denote Z(x,y,z) as the Z image, which is calculated as follows, $$Z(x, y, z) = \begin{cases} 0, & \text{if } I_H(x, y, z) \leq 0 \text{ or } I_p(x, y, z) \leq 0 \\ K\left(\frac{I_P(x, y, z)}{I_H(x, y, z)}\right)^{\frac{1}{n}}, & \text{otherwise} \end{cases}$$

In order to obtain the parameters K and n at step 412, an offline calibration procedure is performed as follows. Two materials such as water and Aluminum are scanned. Each set of the dual energy projections corresponding to each material is processed exactly from Step 400 to Step 410 to yield a Z image with K=1 and n=1. Denote $Z_p^w(x,y,z)$ as the Z image for water, and $Z_p^a(x, y, z)$ as the Z image for Aluminum. The region of interest can be bounding box containing water or Aluminum only, that is, the region of interest for water is $x_l^w \leq x \leq x_u^w$, $y_l^w \leq y \leq y_u^w$, $z_l^w \leq z \leq z_u^w$, and the region of interest for Aluminum is $x_l^a \leq x \leq x_u^a$, $y_l^a \leq y \leq y_u^a$, $z_l^a \leq z \leq z_u^a$. The values of the bounding boxes corresponding to the region of interests for each of the Z images are identified manually. Compute the mean values within the region of interest for each material as follows, denoting $\overline{Z}_p^w$ as the mean for water, and $\overline{Z}_p^a$ as the mean for Aluminum, $$\overline{Z}_p^w = \frac{1}{(x_u^w - x_l^w)(y_u^w - y_l^w)(z_u^w - z_l^w)} \sum_{z=z_l^w}^{z_u^w} \sum_{y=y_l^w}^{y_u^w} \sum_{x=x_l^w}^{x_u^w} Z_p^w(x, y, z)$$

$$\overline{Z}_p^a = \frac{1}{(x_u^a - x_l^a)(y_u^a - y_l^a)(z_u^a - z_l^a)} \sum_{z=z_l^a}^{z_u^a} \sum_{y=y_l^a}^{y_u^a} \sum_{x=x_l^a}^{x_u^a} Z_p^a(x, y, z)$$

Denote the known atomic number for water as $Z_t^w$ and for Aluminum as $Z_t^a$, the parameter n is calculated as $$n = \frac{\ln \overline{Z}_p^a - \ln \overline{Z}_p^w}{\ln Z_t^a - \ln Z_t^w}$$

K is then calculated as follows, $$K = \frac{Z_t^w}{\tilde{Z}_p^w} \text{ where}$$

$$\tilde{Z}_p^w = \frac{1}{(x_u^w - x_l^w)(y_u^w - y_l^w)(z_u^w - z_l^w)} \sum_{z=z_l^w}^{z_u^w} \sum_{y=y_l^w}^{y_u^w} \sum_{x=x_l^w}^{x_u^w} (Z_p^w(x, y, z))^{\frac{1}{n}}$$

A system for computing Z images that includes modules configured to implement the above functionality may also be provided. Such a system may include, for projection data of a set of scanned objects acquired using at least two x-ray spectra, media for storing low energy projection data and high energy projection data. The system may include a calibration module configured to calibrate the Z image calculator with at least two materials with known effective atomic numbers.

Modules for computing Z images may be provided that are configured to reconstruct CT images, decompose the high energy projections and low energy projections into the photoelectric projections, reconstruct photoelectric images, and compute Z images.

While this disclosure has been particularly shown and described with references to preferred embodiments thereof, it will be understood by those skilled in the art that various changes in form and details may be made therein without departing from the spirit and scope of the disclosure as defined by the following claims. Such variations include using low energy projections to reconstruct the CT images for computing Z images and using other two or more materials with known Z for calibration.

The invention claimed is:

1. A method of computing Z images from the CT projection data acquired by scanning a set of objects using at least two x-ray spectra, wherein said projection data includes a set of low energy projections and a set of high energy projections, comprising:
   a. reconstructing a CT image from one of the two sets of projections, which are not processed by any decomposition methods;
   b. obtaining the photoelectric projections from the high energy projections and low energy projections without decomposition to Compton projections;
   c. reconstructing a photoelectric image from the photoelectric projections; and
   d. computing the Z image from the photoelectric image and the CT image, without using any Compton images.

2. The method of claim 1, wherein reconstructing said CT image includes reconstructing said CT image from the set of low energy projections.

3. The method of claim 1, wherein reconstructing said CT image includes reconstructing said CT image from the set of high energy projections.

4. The method of claim 1, wherein reconstructing said CT image from one of the two sets of projections includes using nonlinear beam hardening correction.

5. The method of claim 1, wherein computing the Z image from the photoelectric image and the CT image is a function of at least two parameters K and n, wherein K is a factor for scaling the Z image, and n is an exponent of the ratio of the photoelectric image to the CT image.

6. The method of claim 1, wherein obtaining the photoelectric projections from the high energy projections and low energy projections includes using a two-dimensional look-up table to generate the photoelectric projections.

7. The method of claim 5, further including obtaining values for said parameters K and n through a calibration procedure comprising:
   a. scanning at least two different materials with known effective atomic numbers;
   b. reconstructing CT images;
   c. obtaining the photoelectric projections;
   d. reconstructing photoelectric images from the photoelectric projections;
   e. generating the Z images with k=1 and n=1;
   f. obtaining mean Z values for each of the two materials; and
   g. calculating K and n based on the mean Z values and the known effective atomic numbers of the two materials.

8. A system for computing Z images from the projection data acquired by scanning a set of objects using at least two x-ray spectra, wherein said projection data includes a set of low energy projections and a set of high energy projections, comprising:
   a. a reconstruction subsystem constructed and arranged so as to reconstruct CT images from one of the two sets of projections, which are not processed by any decomposition methods;

b. a dual energy decomposition subsystem constructed and arranged so as to obtain the photoelectric projections from low energy projections and high energy projections without decomposition to Compton projections;

c. a reconstruction subsystem constructed and arranged so as to reconstruct photoelectric images from the photoelectric projections; and d. a Z image calculator constructed and arranged so as to compute the Z images from the CT images and the photoelectric images, without using any Compton images.

9. The system of claim 8, wherein the reconstruction subsystem is constructed and arranged so that said CT image can be reconstructed from the set of low energy projections.

10. The system of claim 8, wherein the reconstruction subsystem is constructed and arranged so that said CT image can be reconstructed from the set of high energy projections.

11. The system of claim 8, wherein said reconstruction subsystem for reconstructing CT images from one of the two sets of projections comprises a module for providing non-linear beam hardening correction.

12. The system of claim 8, wherein said Z image calculator is constructed and arranged so as to compute the Z images from the photoelectric image and the CT image is a function of at least two parameters K and n, wherein K is a factor for scaling the Z image, and n is an exponent of the ratio of the photoelectric image to the CT image.

13. The system of claim 8, wherein the dual energy decomposition subsystem includes a two-dimensional look-up table configured and arranged so as to generate the photoelectric projections.

14. The system of claim 12, wherein said system further includes a calibration module constructed and arranged so as to obtain parameters K and n for the Z image calculator.

* * * * *